(12) United States Patent
Fujisaki et al.

(10) Patent No.: US 7,488,488 B2
(45) Date of Patent: Feb. 10, 2009

(54) TICK CHITINASE

(75) Inventors: Kozo Fujisaki, c/o Obihiro University of Agriculture and Veterinary Medicine National Research Center for Protozoan Diseases, 13 Nishinisen, Inada-cho, Obihiro-shi, Hokkaido 080-8555 (JP); Hideyuki Nagasawa, Hokkaido (JP); Ikuo Igarashi, Hokkaido (JP); Hiroshi Suzuki, Hokkaido (JP); Chihiro Sugimoto, Hokkaido (JP); Gakunan Gen, Hokkaido (JP); Myonjo Yu, Hokkaido (JP); Naotoshi Tsuji, Ibaraki (JP)

(73) Assignees: Meui Seika Kaisha, Ltd., Tokyo (JP); Kozo Fujisaki, Hokkaido (JP)

( * ) Notice: Subject to any disclaimer, the term of this patent is extended or adjusted under 35 U.S.C. 154(b) by 358 days.

(21) Appl. No.: 10/506,010

(22) PCT Filed: Feb. 28, 2003

(86) PCT No.: PCT/JP03/02335

§ 371 (c)(1),
(2), (4) Date: Nov. 19, 2004

(87) PCT Pub. No.: WO03/072609

PCT Pub. Date: Sep. 4, 2003

(65) Prior Publication Data

US 2005/0129702 A1 Jun. 16, 2005

(30) Foreign Application Priority Data

Feb. 28, 2002 (JP) .............................. 2002-053145

(51) Int. Cl.
*A61K 39/02* (2006.01)
(52) U.S. Cl. ................ 424/264.1; 424/234.1; 424/94.1; 435/4; 435/7.4; 530/350
(58) Field of Classification Search .................. 530/350; 424/234.1, 265.1, 94.1; 435/4, 7.4
See application file for complete search history.

(56) References Cited

OTHER PUBLICATIONS

Mikayama et al. (Nov. 1993. Proc.Natl.Acad.Sci. USA, vol. 90 : 10056-10060).*

Rudinger et al. (Jun. 1976. Peptide Hormones. Biol.Council. pp. 5-7).*
Bowie et al., "Deciphering the Message in Protein Sequences: Tolerance to Amino Acid Substitutions," Science, Colume 247, pp. 1306-1310 (1990).*
Murphy et al. Pediatr. Infect. Dis. J. 1989. 8: S66-S68.*
Yamanaka et al (J. Pediatrics. 1993. 122(2): 212-218).*
Fujisaki, K., Development of acquired resistance precipitating antibody in rabbits experimentally infested with females of *Haemaphysalis longicornis* (Ixodoidea: Ixodidae)., Natl. Inst. Anim. Health Q, 1978, vol. 18, No. 1, pp. 27 to 38.
Joelle Le Mao, et al., Mapping of Dermatophagoides farinae mite allergens by two-dimensional immunoblotting., J. Allergy Clin. Immunol., 1998, vol. 102, pp. 631 to 636.
McCall, C., et al., Characterization and cloning of a major high molecular weight house dust mite allergens (Der f 15) for dogs., Vet. Immunol. Immunopathol., 2001, vol. 78, No. 3-4, pp. 231 to 247.
de la Vega H. et al., Chitinases are a multi-gene family•in Aedes, Anopheles and Drosophila., Insect. Mol. Biol., 1998, vol. 7, No. 3, pp. 233 to 239.
Willadsen P. et al., Immunology of the tick-host interaction and the control of ticks and tick-borne diseases., Parasitol Today, 1999, vol. 15, No. 7, pp. 258 to 262.
European Search Report Dated Apr. 25, 2007.
Database UniProt [Online], Oct. 1, 2002, "Chitinase", XP002428764, retrieved from EBI accession No. UNIPROT: Q8MY79, Database accession No. Q8MY79. Database EMBL [Online], Jul. 30, 2002, "*Haemaphysalis longicornis* Cht mRNA for chitinase, complete cds", XP002428765, retrieved from EBI accession No. EMBL: AB074977, Database accession No. AB074977.
Database UniProt [Online], Dec. 1, 2001, "LD45559p", XP002428766, retrieved from EBI accession No. UNIPROT: Q960M0, Database accession No. Q960M0. Database EMBL [Online], Aug. 27, 2001, "Drosophila melanogaster LD45559 full length cDNA", XP002428767, retrieved from EBI accession No. EMBL: AY051988, Database accession No. AY051988.
You, Myungjo, et al., "Identification and Molecular Characterization of a Chitinase from the Hard Tick *Haemaphysalis longicornis*", The Journal of Biological Chemistry, Mar. 7, 2003, pp. 8556-8563, vol. 278, No. 10, XP002428759, ISSN: O021-9258, The American Society for Biochemistry and Molecular Biology, Inc.

* cited by examiner

*Primary Examiner*—Jennifer E Graser
(74) *Attorney, Agent, or Firm*—Sughrue Mion, PLLC

(57) ABSTRACT

A novel chitinase, a polynucleotide encoding the same, a vector and a transformant comprising the polynucleotide, an antibody against the chitinase, and a screening method for screening a substance capable of modifying the chitinase, are disclosed. According to the chitinase, polynucleotide, or vector, it is possible, for example, to exterminate ticks, or to treat or prevent tick-borne infections such as piroplasmosis, Q fever, or viral encephalitis.

3 Claims, 1 Drawing Sheet

F I G. 1
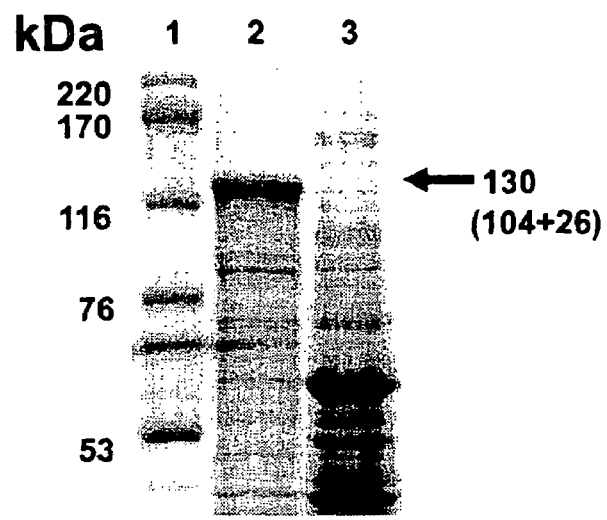
F I G. 2
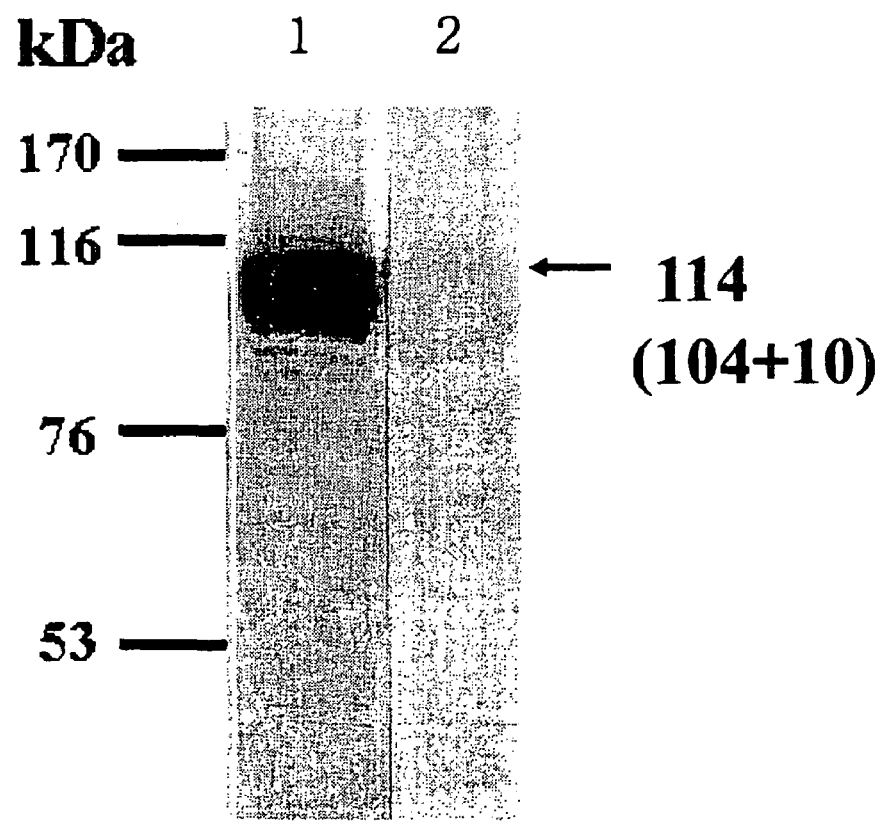

SEQUENCE LISTING

```
<160> NUMBER OF SEQ ID NOS: 8

<210> SEQ ID NO 1
<211> LENGTH: 6439
<212> TYPE: DNA
<213> ORGANISM: Haemaphysalis longicornis
<220> FEATURE:
<221> NAME/KEY: CDS
<222> LOCATION: (571)..(3360)

<400> SEQUENCE: 1
ggtcaggcca gtcgccatac cgctccgtct ggtgcacgag caagtgcatt agagtgtgtg      60
ctccttcgag aaggcgccag caaccggaac tatatccgtc cgggtcctgc agcgtgacta     120
gcgcccaacg tgcgcgaaga cttttgggt agcggagttg ggttgagtgt atcgtctgct     180
tcaagtgggg tcggaggaaa ccgaaaccgt ctgcgcggct cttttgagag cgcgcgccat     240
catcgtctgc agccgagcgt gtctacgacg cgtcttgtcg ccgggtgcgc ttaggtggat     300
accgttcgtc tccctgttcg aaaaaaactt cttgtgcccg tggcctgacc tgcggattga     360
aggcgcttcg cggggactcc gtaggctgat ttttttcccc atcgtgcgga aaaaaaggac     420
accagcgttg gagcaagtgg ttcttttcta gcatcgtgtg tggtaccttg tgagagcgct     480
gtcttcctcg ggttaccgat tctctttccg agcaaggact acgcacccct cactggattc     540
gcgagccttt ctgcgtagag gacatacatc atg aag ccc agg tgg ttc ttc ctg     594
                                   Met Lys Pro Arg Trp Phe Phe Leu
                                     1               5 gcc ttc gtg gcc ctt ttg agc ttc aca aat gtc gtc gac gca agg aga     642
Ala Phe Val Ala Leu Leu Ser Phe Thr Asn Val Val Asp Ala Arg Arg
         10                  15                  20 cca ctc cgg aaa gtc agc ctc aca agt ccg tcg gcg ccg agc ggc ggc     690
Pro Leu Arg Lys Val Ser Leu Thr Ser Pro Ser Ala Pro Ser Gly Gly
 25                  30                  35                  40
```

```
aac acg ggc aag aag atc gtg tgc tac ttc acc aac tgg gcc cag tat         738
Asn Thr Gly Lys Lys Ile Val Cys Tyr Phe Thr Asn Trp Ala Gln Tyr
             45                  50                  55 cga cag ggt gat ggc aag ttt ctg ccg gag gac atc gac ccg acg cta         786
Arg Gln Gly Asp Gly Lys Phe Leu Pro Glu Asp Ile Asp Pro Thr Leu
             60                  65                  70 tgc aca cac atc atc tac gcc ttc ggc tgg atg aag aag cac aag ctg         834
Cys Thr His Ile Ile Tyr Ala Phe Gly Trp Met Lys Lys His Lys Leu
             75                  80                  85 tcg tcc ttc gac gcc gcc gac gac acc aag aac ggc aag aag ggc ctc         882
Ser Ser Phe Asp Ala Ala Asp Asp Thr Lys Asn Gly Lys Lys Gly Leu
 90                  95                 100 tac gag agg gtc att gac ctc aag aag aag aac ccc agt ctc aag gtc         930
Tyr Glu Arg Val Ile Asp Leu Lys Lys Lys Asn Pro Ser Leu Lys Val
105                 110                 115                 120 ctg ctg gcc gtg ggc ggt tgg tcg ttc ggc acg cag cgc ttc aag gag         978
Leu Leu Ala Val Gly Gly Trp Ser Phe Gly Thr Gln Arg Phe Lys Glu
                125                 130                 135 atg gcc tcg aac agc tac aac cgg cgg ctg ttc atc ttc agc gcg ctc        1026
Met Ala Ser Asn Ser Tyr Asn Arg Arg Leu Phe Ile Phe Ser Ala Leu
                140                 145                 150 aac ttc ctg cgc agg cgc aag ttc gac ggt ctc gat ctc gac tgg gag        1074
Asn Phe Leu Arg Arg Arg Lys Phe Asp Gly Leu Asp Leu Asp Trp Glu
                155                 160                 165 ttc ccc cgc gga aac gag gac aag aag aac ttc gtc gaa cta gtc agg        1122
Phe Pro Arg Gly Asn Glu Asp Lys Lys Asn Phe Val Glu Leu Val Arg
                170                 175                 180 gaa ctt cgc gag gca ttc gag gcc gag gcc aaa gag aag aag ctg cca        1170
Glu Leu Arg Glu Ala Phe Glu Ala Glu Ala Lys Glu Lys Lys Leu Pro
185                 190                 195                 200 cga ctg ctg ctc acg gcg gcc gtg tcc gcc ggc gcg gaa acc atc cgg        1218
Arg Leu Leu Leu Thr Ala Ala Val Ser Ala Gly Ala Glu Thr Ile Arg
                205                 210                 215 gga ggc tac gac gtg ccc gcc gtg gcg gcc tac gtg gac ttc ctg aac        1266
Gly Gly Tyr Asp Val Pro Ala Val Ala Ala Tyr Val Asp Phe Leu Asn
                220                 225                 230 gtc atg tcg tac gac ttc cac ggc aag tgg gag agc atg act gga cac        1314
Val Met Ser Tyr Asp Phe His Gly Lys Trp Glu Ser Met Thr Gly His
                235                 240                 245 aac agc ccg ctc tac gcg cag gcc aat gag acc acg tgg cgg aag cag        1362
Asn Ser Pro Leu Tyr Ala Gln Ala Asn Glu Thr Thr Trp Arg Lys Gln
    250                 255                 260 ctg tgc atg gac ttt ggt gtg aaa acc tgg gag cgt ctt ggt gcg ccg        1410
Leu Cys Met Asp Phe Gly Val Lys Thr Trp Glu Arg Leu Gly Ala Pro
265                 270                 275                 280 aag gaa aag atc gtt gtc ggc acg ggc act tac ggc aga acc ttc acc        1458
Lys Glu Lys Ile Val Val Gly Thr Gly Thr Tyr Gly Arg Thr Phe Thr
                285                 290                 295 ttg gcg aat ccc aac aac aat ggc atg aac gcg cca tcg tct ggt ggt        1506
Leu Ala Asn Pro Asn Asn Asn Gly Met Asn Ala Pro Ser Ser Gly Gly
                300                 305                 310 ggt gac gcc gga cag ttc aca aag gaa gct ggc ttc ctt gct tac tac        1554
Gly Asp Ala Gly Gln Phe Thr Lys Glu Ala Gly Phe Leu Ala Tyr Tyr
                315                 320                 325 gag att tgt gat atg ctg aaa aag ggt gcc gac tac gtg tgg gac gag        1602
Glu Ile Cys Asp Met Leu Lys Lys Gly Ala Asp Tyr Val Trp Asp Glu
330                 335                 340 gaa cag ctg gtc ccg tac gcc tac ctc ggc aac caa tgg gtt ggc ttc        1650
Glu Gln Leu Val Pro Tyr Ala Tyr Leu Gly Asn Gln Trp Val Gly Phe
```

```
                                                                -continued
345                  350                   355                    360 gac gac gag aga agc att agg gcc aag atg caa tgg att aag atg aac        1698
Asp Asp Glu Arg Ser Ile Arg Ala Lys Met Gln Trp Ile Lys Met Asn
                365                 370                 375 ggc tac gct gga gcc atg gtc tgg acc gta gac atg gat gat ttt cga        1746
Gly Tyr Ala Gly Ala Met Val Trp Thr Val Asp Met Asp Asp Phe Arg
                380                 385                 390 gga cgc tgc acg acg aaa acg tgg cct ctg att ggc gct atg gcc gag        1794
Gly Arg Cys Thr Thr Lys Thr Trp Pro Leu Ile Gly Ala Met Ala Glu
                395                 400                 405 gaa ttg ctg aac agg cca agt cgg gga cct aaa aat ctg ctg cct ttc        1842
Glu Leu Leu Asn Arg Pro Ser Arg Gly Pro Lys Asn Leu Leu Pro Phe
            410                 415                 420 gtc aag aag cag cgg acg tct agc gcc aag tca acc ggc acc act gaa        1890
Val Lys Lys Gln Arg Thr Ser Ser Ala Lys Ser Thr Gly Thr Thr Glu
425                 430                 435                 440 cca cca aac tcc atc aag gga tcg gac ccg ttg aag gcg gcg cca tcc        1938
Pro Pro Asn Ser Ile Lys Gly Ser Asp Pro Leu Lys Ala Ala Pro Ser
                445                 450                 455 aac ctt ccg gtc aag gac gag gcc cca gaa agt gac acc aac gct cgc        1986
Asn Leu Pro Val Lys Asp Glu Ala Pro Glu Ser Asp Thr Asn Ala Arg
            460                 465                 470 gtc gtc tgc tac ttc acc aac tgg tcc gcc aag cgg aag ggt aag ggc        2034
Val Val Cys Tyr Phe Thr Asn Trp Ser Ala Lys Arg Lys Gly Lys Gly
                475                 480                 485 cac tac gag cca gag gac atc gat gcc acc ctc tgc acg cac gtc atc        2082
His Tyr Glu Pro Glu Asp Ile Asp Ala Thr Leu Cys Thr His Val Ile
            490                 495                 500 tac gcg ttc gcc aac atc aaa gag ttc aag atc gtt ccc acc gag ccc        2130
Tyr Ala Phe Ala Asn Ile Lys Glu Phe Lys Ile Val Pro Thr Glu Pro
505                 510                 515                 520 gtg gat gaa ggc gac ggc agc gcg aag aag ggc ttc tgg gag aga atc        2178
Val Asp Glu Gly Asp Gly Ser Ala Lys Lys Gly Phe Trp Glu Arg Ile
                525                 530                 535 gtg gcc ctg aag act aag aac ccg cag cta aag gtg atg ctc gcc gtc        2226
Val Ala Leu Lys Thr Lys Asn Pro Gln Leu Lys Val Met Leu Ala Val
            540                 545                 550 gga gga tgg atg ctc gga tcc gct ccc ttc agg gag gtc acc gag aac        2274
Gly Gly Trp Met Leu Gly Ser Ala Pro Phe Arg Glu Val Thr Glu Asn
                555                 560                 565 tcc tac agg caa tct ttg ttc gtg ttc aac gcc atc gac ttc ttg agg        2322
Ser Tyr Arg Gln Ser Leu Phe Val Phe Asn Ala Ile Asp Phe Leu Arg
570                 575                 580 gaa aag ggt ttc gat ggt ctc gac gtc gac tgg gag ttt ccc cga ggt        2370
Glu Lys Gly Phe Asp Gly Leu Asp Val Asp Trp Glu Phe Pro Arg Gly
585                 590                 595                 600 gct gag gac aag aag aag ctg gct ggt ctc atc aag gaa ctg aga gtg        2418
Ala Glu Asp Lys Lys Lys Leu Ala Gly Leu Ile Lys Glu Leu Arg Val
                605                 610                 615 gcg ttc gat ggc gag ggc ttg gcg tcc aag aag ccc agg ctc atc ctc        2466
Ala Phe Asp Gly Glu Gly Leu Ala Ser Lys Lys Pro Arg Leu Ile Leu
            620                 625                 630 tcc atg gcg gca ccg gcc agc ttc gag gcc atc tct gcc ggc tac gac        2514
Ser Met Ala Ala Pro Ala Ser Phe Glu Ala Ile Ser Ala Gly Tyr Asp
                635                 640                 645 gtc gag gag ctc aac aag cat gtt gat atg atc aat atg atg acg tac        2562
Val Glu Glu Leu Asn Lys His Val Asp Met Ile Asn Met Met Thr Tyr
650                 655                 660 gac ttc cac gga gac tgg gaa cgt caa gta gga cac cac agc ccc ctg        2610
```

```
Asp Phe His Gly Asp Trp Glu Arg Gln Val Gly His His Ser Pro Leu
665                 670                 675                 680 ttc ccg ctg tac aca gcc agc agt ttc cag aag aag ctt aca gtg gac      2658
Phe Pro Leu Tyr Thr Ala Ser Ser Phe Gln Lys Lys Leu Thr Val Asp
                        685                 690                 695 tac agc gcg ggt gag tgg gtt cgc aag ggg gcc agt aag gaa aag ctg      2706
Tyr Ser Ala Gly Glu Trp Val Arg Lys Gly Ala Ser Lys Glu Lys Leu
                700                 705                 710 ctg gtt ggc att ccc acg tac ggg cgt acc ttc act ctc ggt gac aac      2754
Leu Val Gly Ile Pro Thr Tyr Gly Arg Thr Phe Thr Leu Gly Asp Asn
            715                 720                 725 aac ctg acc gac gtc ggt gct ccg gcc aca gct ggc ggc agg cct ggc      2802
Asn Leu Thr Asp Val Gly Ala Pro Ala Thr Ala Gly Gly Arg Pro Gly
        730                 735                 740 aac tat act ggc gaa act ggg ttc ctg tcc ttt ttc gag atc tgc gac      2850
Asn Tyr Thr Gly Glu Thr Gly Phe Leu Ser Phe Phe Glu Ile Cys Asp
745                 750                 755                 760 ctt ctg cgt tct gga gca acc ctc gta tgg gac aat gag cag atg gtt      2898
Leu Leu Arg Ser Gly Ala Thr Leu Val Trp Asp Asn Glu Gln Met Val
                        765                 770                 775 ccg tac gcc tac aag gac gac cag tgg gtt ggc ttc gac gac cag aga      2946
Pro Tyr Ala Tyr Lys Asp Asp Gln Trp Val Gly Phe Asp Asp Gln Arg
                780                 785                 790 agt ctc aag ctt aag gtc cag tgg ctg aaa cag gcc ggc tac ggc ggg      2994
Ser Leu Lys Leu Lys Val Gln Trp Leu Lys Gln Ala Gly Tyr Gly Gly
            795                 800                 805 gtg atg gtc tgg tcc gta gac ttg gac gac ttc aag ggc acg tgc acg      3042
Val Met Val Trp Ser Val Asp Leu Asp Asp Phe Lys Gly Thr Cys Thr
810                 815                 820 ggc cac agc tac ccg ctg ctt acg gca atc aag gag gag ctc aag gga      3090
Gly His Ser Tyr Pro Leu Leu Thr Ala Ile Lys Glu Glu Leu Lys Gly
825                 830                 835                 840 tac aag gtg gcc aac ctc gaa gtt gcc tct tcc aac ata ctc aac tcg      3138
Tyr Lys Val Ala Asn Leu Glu Val Ala Ser Ser Asn Ile Leu Asn Ser
                845                 850                 855 tac gga cag ctc gtc gat ccg aat gaa gtg gtg tgc gac gaa gag gac      3186
Tyr Gly Gln Leu Val Asp Pro Asn Glu Val Val Cys Asp Glu Glu Asp
                860                 865                 870 ggc cac atc agc tat cac ttg gac aag aag gac tgc acc atg tac tac      3234
Gly His Ile Ser Tyr His Leu Asp Lys Lys Asp Cys Thr Met Tyr Tyr
            875                 880                 885 atg tgc gag gga aag cga cgc cac cac atg ccg tgt ccc act aac ctc      3282
Met Cys Glu Gly Lys Arg Arg His His Met Pro Cys Pro Thr Asn Leu
        890                 895                 900 gta ttt aac tta aac gag agc gtc tgc gac tgg cca gag aat gtg gac      3330
Val Phe Asn Leu Asn Glu Ser Val Cys Asp Trp Pro Glu Asn Val Asp
905                 910                 915                 920 gac tgc aag cat atc gct gct aag acg tag tgtttctgta caacgtttcg        3380
Asp Cys Lys His Ile Ala Ala Lys Thr
                925 ctaacccatt tgccgtcgtc gtgccgtcag cttgccagcg gctgccaggg atcggtttca    3440 ggaagggct aagttgtggc gataaagata tttgcttcgc gattcccttaa ggtggctcgc    3500 actttcaaaa atatcgcttc acccctgcga tctgtgtggg gcattcacta tggagaagtg    3560 tctgtgtcgc atgccgcctt agaaaaacgc gtaattcaac tgacttgaga atttgcttga    3620 aacagtaaag agggcgatat gagcctaaaa agtgccccaa acaagtggc gctctatcac     3680 ggtagctcat gttgcttaac tgttggtgat acgttcccga tcaaaataaa gtcacagcaa    3740
```

```
aataatcgcg attatcaggt ctctgtatga ccgcacaatt aggcgcctaa atattagccg    3800
tgaaaagtta cgacgacggc gaattcgtaa gcggcaattt tgttgttcgg ttctgagtat    3860
tctcttcaca agtgctctca tgtctaaatg cgctcctcac gtgacagaag ccacggagaa    3920 gacgggtct ccttcagcgt accccgcact ggctttggta acatgcctct tgtcacaaa     3980 gctcaatgat gctatatacc caaaacgctg ccaaaaaatc gaaacattac ttgacgctac    4040
ccagtttatt tttacgtact ttgacctcaa aggtacccgt gaagtgccag aaaaaaaat    4100 tctacgccta cgtttgtggg atccagaaat tagtacctca tgagaagcca cacactgtag    4160
tagattttta tatatttggg atacaataaa tgcaatgggg cgttgggctg tgtcaacgt     4220 tttgggggc gccagagtcc gtcagcatac cttcatcttt tcttagtttt ctgaaatcgt    4280
tcgtttgtgt tatgaagagc tcggcttggt agaaatggtc gggctgcaaa tttttaccat    4340
ttgcttcaga gcaatatcgt tgttctttt gttttcgaga aatactacgt gatgttcttt     4400
atttcatcgc agggatgaaa cctttgggaa gagtgtttat ttgtatgaaa agaaaggaag    4460
atgtttgata tgttgcttcc atgttttgtt gcaagtattg tattgtgtac gtcttcagca    4520
ttgttatcac gctcgatcgt ttttaagtag agtagattta tcctggtctt tccagatgtc    4580
aatcataaat atgcgtgttt ttcgaccttt taaaaagtgg tgctatatat atattagagc    4640
aataatagag agggagggta attaggctaa atattcttgc gcgtctatct caaatatttt    4700
ctatcgcctt aaacgaatac cttttctttc aactgaaatg ctctttcttt taaattattg    4760
caaaattcgg tagctctcaa aagtgccttt gcttgtgact aacataacac acacaccgca    4820
agactcgctt tgttaatttc tactttgctg cgcagcacat caaaaacaac aaaatatttt    4880
aaacgtagag aacaactgaa tgcagaacat gtatcacagc tccgcctcct tgtcgtatgg    4940
cgcactcaag tcagttttaa aatattttac gaatgcgaca gcgacattat aatacctatt    5000
acattgcaat gaaagctaaa gtaaatgcaa tatatacttc aaaacgcaag tcctttgttt    5060
tattaggcac tcgtttacac actataaact gataattttt tgttatatcg aggaatactg    5120
taagcaatgc ttgtgtagaa gacaccgatt ttgaacagga actttgaact ctctaggtta    5180
tagtagatga atttatccg taggaaaacg taatacctat cgagtaaata tacaagataa     5240
gaggaaggca cagcagaagc cgtgaaaatg tcaatgtgcc gtgccacacg tttataacct    5300
cctatttgta agttgttctc caatttggta aacttctaaa ctaccgtggc aactctgcaa    5360
aaaacgtgct cattagcatg cgttaacttc attctaaaca ctcagggttg gctcgtattc    5420
gcaacataag gtttcagatc tgatttctgc atgtcaaaag cgccagcaca attttttcgc    5480
caagtgactg cttgtcatgc atatattcgg tgcacacatt tatacagcga tctgctacac    5540
tgcaccgaca agttttattt cgctgtgttt tctgcgcttt tctgtccatg tgtacggcgc    5600
acttcaaata agcaaagcta gcacaaaaac ccgtgcagat gagaaatgta ttcgggcatc    5660
taacattcca aaaatcatcc ggtgacttcg tggtacgctt acgtggttta gacaaatacg    5720
tctcccctat tttgtcgtag cttggagctc agctacacta agaataaaaa agaagcgagc    5780
gttatatttt ccgacagtta cactttcgta cagttgtacg tttgctgcaa cctccttaat    5840
ggctttcaag gccagcacta aacgagcttt tttattatcc tctgttttaaa aaaaatttcg    5900 caaaaaatgg gctcttacaa aaaccaatgc cagaagcatg aagagacaac ggggttatgt    5960
gcataagtgg ttttgcatgg cgggccacat atcttaaata tcacatagcg ccttctttgt    6020
cgtacgatgc ctcctgcagt aagacagcgc ttctctttgc atagcagcga aggcggcgcg    6080
cacatctcga gtattcaaac ggtcttccgc aggtacgctg cgcttgtttt aaggtaacgt    6140
```

```
ctctctaact ttcttattta ttatcacgca taccgcctat gacacttcca gatcgggtgt    6200
gcttatgctt ttattccttg tttgtgtttt ttctctcctt tcttctctac gctgtaccta    6260
ttgcatttga ctgtgtgctt cgagccgtgt gtgcaggtcc cccccacaaa taggagtgga    6320
gagccggcca ctcgtgcttc tgtacaaagt cgcctgccat ctaggagaaa agaaagcga    6380 ataaatacaa acaaaattaa aaaaaaaaaa aaaaaaaaaa aaaaaaaaaa aaaaaaaa      6439

<210> SEQ ID NO 2
<211> LENGTH: 929
<212> TYPE: PRT
<213> ORGANISM: Haemaphysalis longicornis

<400> SEQUENCE: 2
```

| | | | | | | | | | | | | | | | |
|---|---|---|---|---|---|---|---|---|---|---|---|---|---|---|---|
| Met | Lys | Pro | Arg | Trp | Phe | Phe | Leu | Ala | Phe | Val | Ala | Leu | Leu | Ser | Phe |
| 1 | | | | 5 | | | | | 10 | | | | | 15 | |
| Thr | Asn | Val | Val | Asp | Ala | Arg | Arg | Pro | Leu | Arg | Lys | Val | Ser | Leu | Thr |
| | | | 20 | | | | | 25 | | | | | 30 | | |
| Ser | Pro | Ser | Ala | Pro | Ser | Gly | Gly | Asn | Thr | Gly | Lys | Lys | Ile | Val | Cys |
| | | 35 | | | | | 40 | | | | | 45 | | | |
| Tyr | Phe | Thr | Asn | Trp | Ala | Gln | Tyr | Arg | Gln | Gly | Asp | Gly | Lys | Phe | Leu |
| | 50 | | | | | 55 | | | | | 60 | | | | |
| Pro | Glu | Asp | Ile | Asp | Pro | Thr | Leu | Cys | Thr | His | Ile | Ile | Tyr | Ala | Phe |
| 65 | | | | | 70 | | | | | 75 | | | | | 80 |
| Gly | Trp | Met | Lys | Lys | His | Lys | Leu | Ser | Ser | Phe | Asp | Ala | Ala | Asp | Asp |
| | | | | 85 | | | | | 90 | | | | | 95 | |
| Thr | Lys | Asn | Gly | Lys | Lys | Gly | Leu | Tyr | Glu | Arg | Val | Ile | Asp | Leu | Lys |
| | | | 100 | | | | | 105 | | | | | 110 | | |
| Lys | Lys | Asn | Pro | Ser | Leu | Lys | Val | Leu | Leu | Ala | Val | Gly | Gly | Trp | Ser |
| | | | 115 | | | | | 120 | | | | | 125 | | |
| Phe | Gly | Thr | Gln | Arg | Phe | Lys | Glu | Met | Ala | Ser | Asn | Ser | Tyr | Asn | Arg |
| | | 130 | | | | | 135 | | | | | 140 | | | |
| Arg | Leu | Phe | Ile | Phe | Ser | Ala | Leu | Asn | Phe | Leu | Arg | Arg | Arg | Lys | Phe |
| 145 | | | | | 150 | | | | | 155 | | | | | 160 |
| Asp | Gly | Leu | Asp | Leu | Asp | Trp | Glu | Phe | Pro | Arg | Gly | Asn | Glu | Asp | Lys |
| | | | | 165 | | | | | 170 | | | | | 175 | |
| Lys | Asn | Phe | Val | Glu | Leu | Val | Arg | Glu | Leu | Arg | Glu | Ala | Phe | Glu | Ala |
| | | | 180 | | | | | 185 | | | | | 190 | | |
| Glu | Ala | Lys | Glu | Lys | Lys | Leu | Pro | Arg | Leu | Leu | Leu | Thr | Ala | Ala | Val |
| | | | 195 | | | | | 200 | | | | | 205 | | |
| Ser | Ala | Gly | Ala | Glu | Thr | Ile | Arg | Gly | Gly | Tyr | Asp | Val | Pro | Ala | Val |
| | | 210 | | | | | 215 | | | | | 220 | | | |
| Ala | Ala | Tyr | Val | Asp | Phe | Leu | Asn | Val | Met | Ser | Tyr | Asp | Phe | His | Gly |
| 225 | | | | | 230 | | | | | 235 | | | | | 240 |
| Lys | Trp | Glu | Ser | Met | Thr | Gly | His | Asn | Ser | Pro | Leu | Tyr | Ala | Gln | Ala |
| | | | | 245 | | | | | 250 | | | | | 255 | |
| Asn | Glu | Thr | Thr | Trp | Arg | Lys | Gln | Leu | Cys | Met | Asp | Phe | Gly | Val | Lys |
| | | | 260 | | | | | 265 | | | | | 270 | | |
| Thr | Trp | Glu | Arg | Leu | Gly | Ala | Pro | Lys | Glu | Lys | Ile | Val | Val | Gly | Thr |
| | | | 275 | | | | | 280 | | | | | 285 | | |
| Gly | Thr | Tyr | Gly | Arg | Thr | Phe | Thr | Leu | Ala | Asn | Pro | Asn | Asn | Asn | Gly |
| | | 290 | | | | | 295 | | | | | 300 | | | |
| Met | Asn | Ala | Pro | Ser | Ser | Gly | Gly | Gly | Asp | Ala | Gly | Gln | Phe | Thr | Lys |
| 305 | | | | | 310 | | | | | 315 | | | | | 320 |

```
Glu Ala Gly Phe Leu Ala Tyr Tyr Glu Ile Cys Asp Met Leu Lys Lys
                325                 330                 335

Gly Ala Asp Tyr Val Trp Asp Glu Glu Gln Leu Val Pro Tyr Ala Tyr
            340                 345                 350

Leu Gly Asn Gln Trp Val Gly Phe Asp Asp Glu Arg Ser Ile Arg Ala
        355                 360                 365

Lys Met Gln Trp Ile Lys Met Asn Gly Tyr Ala Gly Ala Met Val Trp
    370                 375                 380

Thr Val Asp Met Asp Asp Phe Arg Gly Arg Cys Thr Thr Lys Thr Trp
385                 390                 395                 400

Pro Leu Ile Gly Ala Met Ala Glu Glu Leu Leu Asn Arg Pro Ser Arg
                405                 410                 415

Gly Pro Lys Asn Leu Leu Pro Phe Val Lys Lys Gln Arg Thr Ser Ser
            420                 425                 430

Ala Lys Ser Thr Gly Thr Thr Glu Pro Pro Asn Ser Ile Lys Gly Ser
        435                 440                 445

Asp Pro Leu Lys Ala Ala Pro Ser Asn Leu Pro Val Lys Asp Glu Ala
    450                 455                 460

Pro Glu Ser Asp Thr Asn Ala Arg Val Val Cys Tyr Phe Thr Asn Trp
465                 470                 475                 480

Ser Ala Lys Arg Lys Gly Lys Gly His Tyr Glu Pro Glu Asp Ile Asp
                485                 490                 495

Ala Thr Leu Cys Thr His Val Ile Tyr Ala Phe Ala Asn Ile Lys Glu
            500                 505                 510

Phe Lys Ile Val Pro Thr Glu Pro Val Asp Glu Gly Asp Gly Ser Ala
        515                 520                 525

Lys Lys Gly Phe Trp Glu Arg Ile Val Ala Leu Lys Thr Lys Asn Pro
    530                 535                 540

Gln Leu Lys Val Met Leu Ala Val Gly Gly Trp Met Leu Gly Ser Ala
545                 550                 555                 560

Pro Phe Arg Glu Val Thr Glu Asn Ser Tyr Arg Gln Ser Leu Phe Val
                565                 570                 575

Phe Asn Ala Ile Asp Phe Leu Arg Glu Lys Gly Phe Asp Gly Leu Asp
            580                 585                 590

Val Asp Trp Glu Phe Pro Arg Gly Ala Glu Asp Lys Lys Lys Leu Ala
        595                 600                 605

Gly Leu Ile Lys Glu Leu Arg Val Ala Phe Asp Gly Glu Gly Leu Ala
    610                 615                 620

Ser Lys Lys Pro Arg Leu Ile Leu Ser Met Ala Ala Pro Ala Ser Phe
625                 630                 635                 640

Glu Ala Ile Ser Ala Gly Tyr Asp Val Glu Glu Leu Asn Lys His Val
                645                 650                 655

Asp Met Ile Asn Met Met Thr Tyr Asp Phe His Gly Asp Trp Glu Arg
            660                 665                 670

Gln Val Gly His His Ser Pro Leu Phe Pro Leu Tyr Thr Ala Ser Ser
        675                 680                 685

Phe Gln Lys Lys Leu Thr Val Asp Tyr Ser Ala Gly Glu Trp Val Arg
    690                 695                 700

Lys Gly Ala Ser Lys Glu Lys Leu Leu Val Gly Ile Pro Thr Tyr Gly
705                 710                 715                 720

Arg Thr Phe Thr Leu Gly Asp Asn Asn Leu Thr Asp Val Gly Ala Pro
                725                 730                 735

Ala Thr Ala Gly Gly Arg Pro Gly Asn Tyr Thr Gly Glu Thr Gly Phe
```

-continued

```
                    740                 745                 750
Leu Ser Phe Phe Glu Ile Cys Asp Leu Leu Arg Ser Gly Ala Thr Leu
        755                 760                 765
Val Trp Asp Asn Glu Gln Met Val Pro Tyr Ala Tyr Lys Asp Asp Gln
    770                 775                 780
Trp Val Gly Phe Asp Asp Gln Arg Ser Leu Lys Leu Lys Val Gln Trp
785                 790                 795                 800
Leu Lys Gln Ala Gly Tyr Gly Gly Val Met Val Trp Ser Val Asp Leu
                805                 810                 815
Asp Asp Phe Lys Gly Thr Cys Thr Gly His Ser Tyr Pro Leu Leu Thr
            820                 825                 830
Ala Ile Lys Glu Glu Leu Lys Gly Tyr Lys Val Ala Asn Leu Glu Val
        835                 840                 845
Ala Ser Ser Asn Ile Leu Asn Ser Tyr Gly Gln Leu Val Asp Pro Asn
    850                 855                 860
Glu Val Val Cys Asp Glu Asp Gly His Ile Ser Tyr His Leu Asp
865                 870                 875                 880
Lys Lys Asp Cys Thr Met Tyr Tyr Met Cys Glu Gly Lys Arg Arg His
                885                 890                 895
His Met Pro Cys Pro Thr Asn Leu Val Phe Asn Leu Asn Glu Ser Val
            900                 905                 910
Cys Asp Trp Pro Glu Asn Val Asp Asp Cys Lys His Ile Ala Ala Lys
        915                 920                 925
Thr
```

<210> SEQ ID NO 3
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 3
acgaattcca tcatgaagcc cagg                                          24

<210> SEQ ID NO 4
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 4
acctcgagct acgtcttagc agcg                                          24

<210> SEQ ID NO 5
<211> LENGTH: 13
<212> TYPE: PRT
<213> ORGANISM: Aedes aegypti

<400> SEQUENCE: 5

```
Lys Val Thr Leu Ala Ile Gly Gly Trp Asn Asp Ser Ala
1               5                   10
```

<210> SEQ ID NO 6
<211> LENGTH: 13
<212> TYPE: PRT
<213> ORGANISM: Aedes aegypti

<400> SEQUENCE: 6

```
Tyr Gly Phe Asp Gly Leu Asp Leu Asp Trp Glu Tyr Pro
1               5                   10
```

```
<210> SEQ ID NO 7
<211> LENGTH: 16
<212> TYPE: DNA
<213> ORGANISM: Artificial Sequence
<220> FEATURE:
<223> OTHER INFORMATION: An artificially synthesized primer sequence

<400> SEQUENCE: 7
tggkcvrtst aycgdc                                                     16

<210> SEQ ID NO 8
<211> LENGTH: 20
<212> TYPE: DNA
<213> ORGANISM: Artificial Sequence
<220> FEATURE:
<223> OTHER INFORMATION: An artificially synthesized primer sequence
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 8
ccartcrakr tcnadnccvt                                                 20
```

TICK CHITINASE

TECHNICAL FIELD

This invention relates to a tick chitinase.

BACKGROUND ART

Ticks are the cause, directly or indirectly, of extensive damage to animals or humans. Examples of the direct damage are pruritus or bleeding caused by biting or blood-sucking, or tick paralysis or allergic diseases caused by saliva secreted in blood-sucking or regurgitation of midgut contents. Examples of the indirect damage are various diseases in livestock, caused by viruses, rickettsiae, bacterium, spirochaeta, protozoa, nematoda, or the like. This damage causes enormous losses at home and abroad, and threat of emerging and re-emerging zoonotic diseases by ticks is becoming a serious problem.

Under these circumstances, various methods to exterminate ticks are used in many countries. Among these methods, the major one is the use of agents such as organic phosphorus agents, carbamate agents, pyrethroid or macrolide antibiotics, or the like. However, in any agent, a drug resistance is established by using the agent successively or heavily, and thus many agents lose their miticidal activity. Further, when using such agents, it is necessary to take side effects to animals into consideration. In addition, there is a problem of a remnant agent which may threaten the safety of foods and the environment, and people tend to avoid the use of such agents. Furthermore, the use of agents is approaching limitation, with respect to the enormous development cost, in addition to the effectiveness thereof and an applicable area. As described above, it is considered difficult to prevent the parasitism of ticks to humans or animals, and the damage caused by ticks-borne infection in the 21st century, by means of the use of agents.

In hematophagous arthropods including ticks, acquisition of protective immune response against reinfection in a host against a viral or bacterial infection is known and has been confirmed in the laboratory stage [Fujisaki, Nat. Inst. Anim. Hlth. Quart. (Tokyo), 18, 27-38 (1978)]. Due to the recent progress in gene recombination techniques, genes encoding protective antigens, enzymes related to metamorphosis specific to hematophagous arthropods, or the like are being intensively cloned in many countries, and an attempt to manufacture safe vaccine proteins or chemotherapeutic agents has been made.

However, such an agent in practical use is only that against Boophilus microplus, which was developed by Willadesen [Willadesen and Jogejan, Prasitology Today. 15, 258-262 (1999)]. There is now a search for a vaccine against *Haemaphysalis longicornis*, which is widely distributed over Asian countries including Japan and the Eurasia continent and mediates zoonotic diseases such as piroplasmosis, Q fever, or viral encephalitis and thus the rapid development and practical application of such a vaccine is greatly desired.

DISCLOSURE OF INVENTION

The present inventors have conducted intensive studies into obtaining a novel polypeptide useful as a candidate for a vaccine against ticks, particularly *Haemaphysalis longicornis*, and a polynucleotide encoding the polypeptide and, as a result, found a novel chitinase and a polynucleotide encoding the same. Further, the present inventors inoculated the chitinase into mice, to observe the induction of an antibody production, and confirmed that the chitinase is useful as a tick vaccine. The present invention is based on the above findings.

The object of the present invention is to provide a novel chitinase useful as a tick vaccine, and a polynucleotide encoding the chitinase.

The object can be solved by a polypeptide of the present invention, i.e., (1) a polypeptide consisting of the amino acid sequence of SEQ ID NO: 2;

(2) a polypeptide comprising the amino acid sequence of SEQ ID NO: 2 and exhibiting a chitinase activity;

(3) a polypeptide exhibiting a chitinase activity and comprising an amino acid sequence in which one or plural amino acids are substituted, deleted, and/or inserted at one or plural positions in the amino acid sequence of SEQ ID NO: 2; or (4) a polypeptide comprising an amino acid sequence having a 60% or more homology with the amino acid sequence of SEQ ID NO: 2, and exhibiting a chitinase activity.

The present invention relates to a polynucleotide encoding the polypeptide.

The present invention relates to a vector comprising the polynucleotide.

The present invention relates to a transformant comprising the polynucleotide.

The present invention relates to a process for producing the polypeptide, comprising the step of culturing the transformant.

The present invention relates to a medicament comprising the polypeptide or a fragment thereof, the polynucleotide, or the vector.

The present invention relates to a pharmaceutical composition comprising the polypeptide or a fragment thereof, the polynucleotide, or the vector, and a pharmaceutically or veterinary acceptable carrier or diluent.

The present invention relates to a method for exterminating ticks, comprising administering to a subject in need thereof the polypeptide or a fragment thereof, the polynucleotide, or the vector in an amount effective therefor.

The present invention relates to a method for treating or preventing a tick-borne infection, comprising administering to a subject in need thereof the polypeptide or a fragment thereof, the polynucleotide, or the vector in an amount effective therefor.

The present invention relates to an antibody or a fragment thereof, which binds to the polypeptide.

The present invention relates to a method for screening a substance capable of modifying a chitinase activity of the polypeptide, comprising the steps of:

bringing the polypeptide into contact with a substance to be tested; and analyzing the chitinase activity of the polypeptide.

BRIEF DESCRIPTION OF DRAWINGS

FIG. 1 shows the result of SDS-polyacrylamide gel electrophoresis of a recombinant chitinase fusion protein.

FIG. 2 shows the result of electrophoresis of native (wild type) chitinase in a tick egg lysate by immunoblotting.

BEST MODE FOR CARRYING OUT THE INVENTION

The present invention will be explained in detail hereinafter.

[1] Polypeptide of the Present Invention

The polypeptides of the present invention includes
(1) a polypeptide consisting of the amino acid sequence of SEQ ID NO: 2;
(2) a polypeptide comprising the amino acid sequence of SEQ ID NO: 2 and exhibiting a chitinase activity;
(3) a polypeptide comprising an amino acid sequence in which one or plural amino acids are substituted, deleted, and/or inserted at one or plural positions in the amino acid sequence of SEQ ID NO: 2, and exhibiting a chitinase activity (hereinafter referred to as a variation functionally equivalent); and
(4) a polypeptide comprising an amino acid sequence having a 60% or more homology with the amino acid sequence of SEQ ID NO: 2, and exhibiting a chitinase activity (hereinafter referred to as a homologous polypeptide).

The term "chitinase activity" as used herein means an enzyme activity in which chitin [poly(β-1,4-N-acetyl D-glucosamine)] is digested to generate oligosaccharides and N-acetylglucosamine. Whether or not a polypeptide to be tested exhibits the chitinase activity may be easily confirmed, for example, by a known method for measuring the chitinase activity, in which the polypeptide to be tested is brought into contact with a substrate of chitinase, and then the digestion and/or a degree thereof of the chitinase substrate is analyzed [for example, Johannes et al., Infect. Immun., 69, 4041-4047 (2001)]. The method is not particularly limited, but is preferably confirmed by a method described in Example 6.

More particularly, for example, a polypeptide to be tested is added to a well of an agarose gel containing an appropriate substrate of chitinase (for example, glycol chitin or chitin), and incubated for a predetermined period (for example, at 37° C. for 12 hours). The gel is stained with an appropriate dye [for example, Fluorescent Brightener 28 (Sigma)] and observed under an ultraviolet ray. The portion in which chitin is digested by chitinase does not react with the dye, and becomes black. In this case, it may be judged that the polypeptide to be tested exhibits the chitinase activity. Conversely, when the chitinase reaction does not occur, the gel is brightened by the reaction with the dye. In this case, it may be judged that the polypeptide to be tested does not exhibit the chitinase activity.

The "polypeptide comprising the amino acid sequence of SEQ ID NO: 2 and exhibiting the chitinase activity" as the polypeptide of the present invention includes, for example,
a fusion polypeptide consisting of an amino acid sequence in which an appropriate marker sequence or the like is added to the N-terminus and/or the C-terminus of the amino acid sequence of SEQ ID NO: 2, and exhibiting the chitinase activity; or
a fusion polypeptide of the polypeptide consisting of the amino acid sequence of SEQ ID NO: 2 and a partner for fusion, and exhibiting the chitinase activity.

As the marker sequence, for example, a sequence for easily carrying out a confirmation of polypeptide expression, a confirmation of intracellular localization thereof, a purification thereof, or the like may be used. As the sequence, there may be mentioned, for example, a FLAG tag, a hexa-histidine tag, a hemagglutinin tag, a myc epitope, or the like.

As the partner for fusion, there may be mentioned, for example, a polypeptide for purification [for example, glutathione S-transferase (GST) or a fragment thereof], a polypeptide for detection [for example, hemagglutinin or β-galactosidase α peptide (LacZ α), or a fragment thereof], a polypeptide for expression (for example, a signal sequence), or the like.

In the above fusion polypeptide, an amino acid sequence which can be specifically digested with a protease such as thrombin or factor Xa may be optionally inserted between the polypeptide consisting of the amino acid sequence of SEQ ID NO: 2 and the marker sequence or the partner for fusion.

The variation functionally equivalent of the present invention is not particularly limited, so long as it is a polypeptide comprising an amino acid sequence in which one or plural (preferably 1 to 10, more preferably 1 to 7, most preferably 1 to 5) amino acids in total (for example, one to several amino acids in total) are deleted, substituted, and/or inserted at one or plural positions in the amino acid sequence of SEQ ID NO: 2, and exhibiting the chitinase activity. Further, an origin of the variation functionally equivalent is not limited to *Haemaphysalis longicornis*.

The variation functionally equivalent of the present invention includes not only *Haemaphysalis longicornis* variations of the polypeptide consisting of the amino acid sequence of SEQ ID NO: 2, but also variations functionally equivalent derived from organisms other than *Haemaphysalis longicornis* [for example, Ixodids (hard ticks) other than *Haemaphysalis longicornis*, or Argasids (soft ticks)]. Further, it includes polypeptides prepared using polynucleotides obtained by artificially modifying their amino acid sequences encoded thereby by genetic engineering techniques, on the basis of polynucleotides encoding these native polypeptides (i.e., *Haemaphysalis longicornis* variations or variations functionally equivalent derived from organisms other than *Haemaphysalis longicornis*), or on the basis of polynucleotides encoding the amino acid sequence of SEQ ID NO: 2. The term "variation" as used herein means an individual difference between the same polypeptides in the same species or a difference between homologous polypeptides in several species.

*Haemaphysalis longicornis* variations of the polypeptide consisting of the amino acid sequence of SEQ ID NO: 2, or variations functionally equivalent derived from organisms other than *Haemaphysalis longicornis* may be obtained by those skilled in the art in accordance with the information of a base sequence (for example, the base sequence of the 571st to 3360th bases in the base sequence of SEQ ID NO: 1) of a polynucleotide encoding the polypeptide consisting of the amino acid sequence of SEQ ID NO: 2. In this connection, genetic engineering techniques may be generally performed in accordance with known methods (for example, Sambrook et al., "Molecular Cloning, A Laboratory Manual", Cold Spring Harbor Laboratory Press, 1989), unless otherwise specified.

For example, an appropriate probe or appropriate primers are designed in accordance with the information of a base sequence of a polynucleotide encoding the polypeptide consisting of the amino acid sequence of SEQ ID NO: 2. A polymerase chain reaction (PCR) method (Saiki, R. K. et al., Science, 239, 487-491, 1988) or a hybridization method is carried out using a sample (for example, total RNA or an mRNA fraction, a cDNA library, or a phage library) derived prepared from an organism [for example, Ixodids (hard ticks) other than *Haemaphysalis longicornis*, or Argasids (soft ticks)] of interest and the primers or the probe to obtain a polynucleotide encoding the polypeptide. A desired polypeptide may be obtained by expressing the resulting polynucleotide in an appropriate expression system and confirming that the expressed polypeptide exhibits the chitinase activity by, for example, the method described in Example 6.

Further, the polypeptide artificially modified by genetic engineering techniques may be obtained by, for example, the following procedure. A gene encoding the polypeptide is obtained by a conventional method such as site-specific directed mutagenesis (Mark, D. F. et al., Proc. Natl. Acad. Sci. USA, 81, 5662-5666, 1984). A desired polypeptide may be obtained by expressing the resulting polynucleotide in an appropriate expression system and confirming that the expressed polypeptide exhibits the chitinase activity by, for example, the method described in Example 6.

The homologous polypeptide of the present invention is not particularly limited, so long as it is a polypeptide having an amino acid sequence having a 60% or more homology with the amino acid sequence of SEQ ID NO: 2, and exhibiting the chitinase activity. The homologous polypeptide of the present invention may have an amino acid sequence having preferably a 70% or more homology, more preferably a 80% or more homology, more preferably a 90% or more homology, more preferably a 95% or more homology, most preferably a 98% or more homology, with respect to the amino acid sequence of SEQ ID NO: 2. The term "homology" as used herein means a value obtained by a Clustal program (Higgins and Sharp, Gene, 73, 237-244, 1988; and Thompson et al., Nucleic Acid Res., 22, 4673-4680, 1994) in accordance with a default parameter.

The above-mentioned novel polypeptide of the present invention may be manufactured by various known methods, for example, known genetic engineering techniques using the polynucleotide of the present invention which encodes the polypeptide of the present invention. More particularly, the polypeptide of the present invention may be prepared by culturing the transformant of the present invention described below (i.e., the transformant comprising the polynucleotide of the present invention) under conditions in which the novel polypeptide of the present invention can be expressed, and then separating and purifying the desired polypeptide from the resulting culture in accordance with a conventional method for a polypeptide separation and purification. As the separation and purification method, there may be mentioned, for example, salting-out with ammonium sulfate, an ion exchange column chromatography using ion exchange cellulose, a molecular sieve column chromatography using molecular sieve gel, an affinity column chromatography using protein A agarose, dialysis, lyophilization, or the like.

The present invention includes a fragment of the polypeptide of the present invention. The fragment of the present invention is useful as an active ingredient for the medicament of the present invention or as an antigen for preparing the antibody of the present invention.

[2] Polynucleotide of the Present Invention

The polynucleotide of the present invention is not particularly limited, so long as it encodes the polypeptide of the present invention. As the polynucleotide of the present invention, there may be mentioned, for example, a polynucleotide consisting of the 571st to 3360th bases in the base sequence of the SEQ ID NO: 1. In this connection, the term "polynucleotide" as used herein includes both DNA and RNA.

The present invention includes a polynucleotide comprising a base sequence which can hybridize with the polynucleotide of the present invention, preferably a polynucleotide consisting of a base sequence which can hybridize with the polynucleotide of the present invention. The base sequence capable of hybridizing with the polynucleotide of the present invention is preferably a base sequence complementary to the base sequence (or a partial sequence thereof) of the polynucleotide of the present invention, more preferably a base sequence complementary to the base sequence (or a partial sequence thereof) consisting of the 571st to 3360th bases in the base sequence of the SEQ ID NO: 1.

[3] Vector and Transformant of the Present Invention

The vector of the present invention is not particularly limited, so long as it comprises the polynucleotide of the present invention. As the vector, there may be mentioned, for example, a vector obtained by introducing the polynucleotide of the present invention into a known expression vector appropriately selected in accordance with a host cell to be used.

The transformant of the present invention is not particularly limited, so long as it comprises the polynucleotide of the present invention. The transformant of the present invention may be, for example, a cell in which the polynucleotide is integrated into a chromosome of a host cell, or a transformant containing the polynucleotide as a vector comprising polynucleotide. Further, the transformant of the present invention may be a transformant expressing the polypeptide of the present invention, or a transformant not expressing the polypeptide of the present invention. The transformant of the present invention may be obtained by, for example, transfecting a desired host cell with the vector of the present invention or the polynucleotide of the present invention per se.

The host cell may be, for example, a known microorganism usually used, for example, an *Escherichia coli* or yeast (*Saccharomyces cerevisiae*), or a known cultivated cell, such as an animal cell, such as a CHO cell, an HEK-293 cell, or a COS cell, or an insect cell such as a BmN4 cell.

The known expression vector may be, for example, pUC, pTV, pGEX, pKK, or pTrcHis for an *Escherichia coli*; pEM-BLY or pYES2 for the yeast; pcDNA3 or pMAMneo for the CHO cell; pcDNA3 for the HEK-293 cell; pcDNA3 for the COS cell; a vector (such as pBK283) containing a polyhedrin promoter of a silkworm nucleopolyhederovirus (BmNPV) for the BmN4 cell. Further, the expression vector includes a virus vector which can be used as a vector for a gene therapy, such as retrovirus, adenovirus, or Sendai virus.

[4] Medicament of the Present Invention

The medicament of the present invention (preferably a tick vaccine) comprises, as a active ingredient, the polypeptide of the present invention or a fragment thereof, the polynucleotide of the present invention, or the vector of the present invention. In the present invention, the polypeptide of the present invention or a fragment thereof, the polynucleotide of the present invention, or the vector of the present invention can be orally or parenterally administered alone, or preferably together with a pharmaceutically or veterinarily acceptable carrier or diluent, to an animal (preferably a mammal, particularly a human) in need of an extermination of ticks.

When the active ingredient in the medicament of the present invention (i.e., the polypeptide of the present invention or a fragment thereof, the polynucleotide of the present invention, or the vector of the present invention) is administered to an animal as a tick vaccine, an antibody production may be induced and then ticks may be terminated by protective immune response against reinfection in the host animal. Further, as a result, it is possible to treat or prevent tick-borne infections such as piroplasmosis, Q fever, or viral encephalitis.

In other words, the pharmaceutical composition (preferably pharmaceutical composition for exterminating ticks or pharmaceutical composition for treating or preventing a tick-borne infection) of the present invention comprises the polypeptide of the present invention or a fragment thereof, the polynucleotide of the present invention, or the vector of the present invention as the active ingredient, and a pharmaceutically or veterinary acceptable carrier or diluent. The active ingredient in the present invention (i.e., the polypeptide of the present invention or a fragment thereof, the polynucleotide of the present invention, or the vector of the present invention) can be used in the manufacture of the above medicament (preferably medicament for exterminating ticks or medicament for treating or preventing a tick-borne infection).

When the medicament of the present invention is used as a tick vaccine, the fragment of the polypeptide of the present invention is not particularly limited, so long as the fragment administered to a subject can induce immunity thereagainst. The fragment can be appropriately selected by those skilled in the art.

The medicament (particularly the tick vaccine) of the present invention can be used, for example, by mixing the polypeptide of the present invention with an adjuvant or the like and inoculating the resulting mixture into an animal (for example, livestock) at an appropriate interval as a tick vaccine. Further, it can be used by dissolving or suspending the polypeptide of the present invention directly in an appropriate solvent, or by enclosing it in liposomes or integrating a DNA encoding it in an appropriate vector. Furthermore, it can be used in an appropriate formulation such as injections, tablets, capsules, eye drops, creams, suppositories, sprays, poultices, or the like, optionally by adding a pharmaceutical acceptable carrier to the polypeptide of the present invention.

As the pharmaceutical acceptable carrier, well-known solvents, bases, stabilizing agents, antiseptics, solubilizing agents, fillers, buffers, and the like may be used. When the polypeptide of the present invention contained in the medicament of the present invention is used in the above formulation, the administration method and the dose may be determined in accordance with, for example, the age or sex of each subject, or the kind or degree of each disease.

The oral administration includes a sublingual administration. As the parenteral administration, for example, inhalation, percutaneous administration, ophthalmic administration, vaginal administration, intra-articular administration, rectal administration, intra-arterial administration, intravenous administration, local administration, intramuscular administration, subcutaneous administration, intraperitoneal administration, or the like may be selected.

[5] Antibody and the Fragment thereof of the Present Invention

An antibody, such as a polyclonal antibody or a monoclonal antibody, which reacts with the polypeptide of the present invention may be obtained by directly administering the polypeptide of the present invention or a fragment thereof to various animals. Alternatively, it may be obtained by a DNA vaccine method (Raz, E. et al., Proc. Natl. Acad. Sci. USA, 91, 9519-9523, 1994; or Donnelly, J. J. et al., J. Infect. Dis., 173, 314-320, 1996), using a plasmid into which a polynucleotide encoding the polypeptide of the present invention is inserted.

The polyclonal antibody may be produced from a serum or eggs of an animal such as a rabbit, a rat, a goat, or a chicken, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody may be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody may be easily produced by those skilled in the art, according to, for example, a cell fusion method of Kohler and Milstein (Kohler, G. and Milstein, C., Nature, 256, 495-497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) may be used. As a fusing agent, polyethylene glycol may be used. As a medium for preparation of hybridomas, for example, a commonly used medium such as an Eagle's minimum essential medium, a Dulbecco's modified minimum essential medium, or an RPMI-1640 medium may be used by adding properly 10 to 30% of a fetal bovine serum. The fused strains may be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which may be purified are produced by culturing the resulting hybridomas in a medium for 2 to 4 days, or in the peritoneal cavity of a pristane-pretreated BALB/c strain mouse for 10 to 20 days.

The resulting monoclonal antibodies in the culture supernatant or the ascites may be separated and purified by conventional polypeptide isolation and purification methods. Examples of the separation and purification methods include, for example, centrifugal separation, dialysis, salting-out with ammonium sulfate, or chromatographic technique using such as DEAE-cellulose, hydroxyapatite, protein A agarose, and the like.

Further, the monoclonal antibodies or the antibody fragments containing a part thereof may be produced by inserting the whole or a part of a gene encoding the monoclonal antibody into an expression vector and introducing the resulting expression vector into appropriate host cells (such as *E. coli*, yeast, or animal cells).

Antibody fragments comprising an active part of the antibody such as F(ab')$_2$, Fab, Fab', or Fv may be obtained by a conventional method, for example, by digesting the separated and purified antibodies (including polyclonal antibodies and monoclonal antibodies) with a protease such as pepsin, papain, and the like, and separating and purifying the resulting fragments by standard polypeptide isolation and purification methods.

Further, an antibody which reacts to the polypeptide of the present invention may be obtained in a form of single chain Fv or Fab in accordance with a method of Clackson et al. or a method of Zebedee et al. (Clackson, T. et al., Nature, 352, 624-628, 1991; or Zebedee, S. et al., Proc. Natl. Acad. Sci.

USA, 89, 3175-3179, 1992). Furthermore, a humanized antibody may be obtained by immunizing a transgenic mouse in which mouse antibody genes are substituted with human antibody genes (Lonberg, N. et al., Nature, 368, 856-859, 1994).

[6] Screening Method of the Present Invention

It is possible to determine whether or not a substance to be tested modifies (for example, suppresses or promotes) the chitinase activity of the polypeptide according to the present invention, using the polypeptide of the present invention.

Substances to be tested to which may be applied the screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135-8137, 1995), or random peptides prepared by employing a phage display method (Felici, F. et al., J. Mol. Biol., 222, 301-310, 1991) or the like. In addition, culture supernatants of microorganisms, natural components derived from plants or marine organisms, or animal tissue extracts may be used as the test substances for screening. Further, compounds (including peptides) obtained by chemically or biologically modifying compounds (including peptides) selected by the screening method of the present invention may be used.

The screening method of the present invention may be carried out by a method similar to the above-mentioned method for confirming the chitinase activity, except that the polypeptide of the present invention, a substrate of chitinase, and the test substance are brought into contact with each other instead of bringing the test polypeptide into contact with a substrate of chitinase.

Namely, in the screening method of the present invention, it is confirmed whether or not the test substance modifies the chitinase activity of the polypeptide of the present invention by bringing into contact the polypeptide of the present invention, a substrate of chitinase, and the test substance, and then analyzing whether or not the substrate of chitinase is digested (or a degree of the digestion) by the chitinase activity of the polypeptide of the present invention in the presence of the test substance. When the substrate of chitinase is not degraded by the chitinase activity of the polypeptide of the present invention, or the degree of the digestion is decreased, it is possible to confirm that the test substance suppresses the chitinase activity of the polypeptide of the present invention. Alternatively, when the degree of the digestion of the substrate of chitinase by the chitinase activity of the polypeptide of the present invention is increased, it is possible to confirm that the test substance promotes the chitinase activity of the polypeptide of the present invention.

EXAMPLES

The present invention now will be further illustrated by, but is by no means limited to, the following Examples. The procedures described in the following Examples were performed in accordance with various techniques commonly used in molecular biology, acarology, arthropodology, immunology, or biochemistry, described in, for example, Sambrook et al., "Molecular Cloning, A Laboratory Manual", Cold Spring Harbor Laboratory Press, 1989 or similar books. As a software for analyzing DNA, MacVector™ (Oxford Molecular) was used.

Example 1

Isolation of a Gene Encoding a Novel Tick Chitinase

Total RNA was extracted from eggs of a *Haemaphysalis longicornis* Okayama strain [Fujisaki et al., Nat. Inst. Anim. Hlth Quart. (Tokyo), 16, 122-128 (1976)] by an Acid Guanidinium-phenol-chloroform method [Chomczynski et al., Anal. Biochem., 162, 156-159 (1987)]. From the resulting total RNA, poly A+ RNA was purified using an mRNA isolation kit [Oligotex-dT30 (Super), code W9021B; Takara] in accordance with a protocol attached to the kit.

The following procedures, i.e., construction of a cDNA library, screening, and insertion into plasmid of a cDNA clone (in vivo Excision) were performed using commercially available reagent kits (Stratagen) in accordance with protocols attached thereto.

More particularly, cDNA was synthesized using 5 µg of tick mRNA as a template and a cDNA synthesis kit (ZAP-cDNA Synthesis Kit, Cat. No. 200401-5; Stratagen). The resulting cDNA was fractionated by a size fractionation with a Sepharose CL-2B gel column, inserted into a vector (Uni-ZAP XR Vector, Cat. No. 237211; Stratagen), and packaged using a packaging reagent (GigapackIII Gold packaging extract; Stratagen). *Escherichia coli* (*E. coli* XL1-Blue MRF' strain) was transfected with the packaged product to obtain a library containing approximately 500,000 cDNA clones.

The cDNA library was plaque-screened using a polymerase chain reaction (PCR) method, to obtain four overlapping positive clones. More particularly, a fragment of a tick chitinase gene obtained by PCR, as a probe, was reacted with the cDNA library. A positive colony was observed as a black dot. Screening was performed by confirming the black dots. In this connection, the PCR was carried out using two primers having the base sequences of SEQ ID NOS: 7 and 8 designed from the amino acid sequences of SEQ ID NOS: 5 and 6, respectively. In the PCR, 50 µL of a reaction liquid [template DNA 1 µg, 0.1 µmol/L primer, 10 mmol/L Tris-HCl (pH8.3), 50 mmol/L KCl, 1.5 mmol/L $MgCl_2$, and 2.5U Taq Gold DNA polymerase (Part No. N808-0244; Perkin Elmer)] was used, and a cycle composed of treatments at 94° C. for 1 minute, 50° C. for 1 minute, and 72° C. for 2 minutes was repeated 40 times.

These positive clones were inserted into plasmid (i.e., converted into a pBluescript) by an in vivo Excision method.

Each plasmid containing a cDNA fragment was purified using a plasmid purification kit (Cat no. 12125; Qiagen), and then PCR was carried out using a sequencing kit (Dye Primer Cycle Sequencing Kit, Part No. 4303153; Perkin Elmer) in accordance with a protocol attached to the kit. Each resulting PCR product was analyzed with a DNA sequencer (ABI PRISM 3100 Genetic Analyzer; Perkin Elmer) to determine a base sequence of each cDNA fragment.

As a result, it was found that all four clones were derived from a single gene. The longest clone was used in the following analyses.

The full length of the cDNA was 6439 bp, and the base sequence thereof was that of SEQ ID NO: 1. It was confirmed that the base sequence contains an open reading frame consisting of 2790 bp (a base sequence consisting of the 571st to 3360th bases in the base sequence of SEQ ID NO: 1). The amino acid sequence of a protein deduced from the open reading frame was the amino acid sequence of SEQ ID NO: 2 consisting of 929 amino acid residues, and the deduced molecular weight was 104 kDa.

The homology search of the deduced amino acid sequence was carried out by a BLAST method (Basic local alignment search tool; Altschul, S. F. et al., J. Mol. Biol., 215, 403-410, 1990; obtained from the National Center for Biotechnology Information). As a result, it was confirmed that the amino acid sequence had a high homology with known chitinase proteins derived from other organisms. For example, it had an approximately 30% homology with yellow fever mosquito (*Aedes aegypti*) chitinase [Insect Mol. Biol., 7(3), 233-239 (1998)].

Example 2

Construction of Vector for Expressing Tick Chitinase Fusion Protein

For cloning the ORF region of the tick chitinase gene, a DNA amplification was carried out by PCR using the cDNA clone obtained in Example 1 as a template, and a sense primer (consisting of the base sequence of SEQ ID NO: 3 and containing the EcoRI recognition site "gaattc" at the 5' terminus) and an antisense primer (consisting of the base sequence of SEQ ID NO: 4 and containing the XhoI recognition site "ctcgag" at the 5' terminus). In the PCR, 50 μL of a reaction liquid [template DNA 1 μg, 0.1 μmol/L primer, 10 mmol/L Tris-HCl (pH8.3), 50 mmol/L KCl, 1.5 mmol/L $MgCl_2$, and 2.5U Taq Gold DNA polymerase (Part No. N808-0244; Perkin Elmer)] was used, and a cycle composed of treatments at 94° C. for 1 minute, 50° C. for 1 minute, and 72° C. for 2 minutes was repeated 40 times.

The PCR product was treated with phenol/chloroform, collected by an ethanol precipitation method, and dissolved in distilled water. The resulting DNA solution was digested with the restriction enzyme EcoRI, and then the DNA fragment was separated by electrophoresis, purified using a DNA purification kit (Cat no. 1001-400; Biotechnologies), and collected in distilled water.

Meanwhile, a vector pGEMEX-4T-3 (Product no. 27-4583; Pharmacia Biotech) for expression in *Escherichia coli* was digested with the restriction enzyme EcoRI, dephosphorylated with alkaline phosphatase, and purified in the manner similar to that used in the purification of the PCR product.

The purified PCR product and vector were reacted using a DNA ligation kit (Cat no. 6022; Takara) in accordance with a protocol attached to the kit. *Escherichia coli* DH5α was transformed with the ligation reaction product, and then recombinant clones in which the chitinase ORF fragment was inserted in the same direction as that of glutathione S-transferase (GST) in the vector were selected. A recombinant plasmid was purified using a plasmid purification kit (Cat no. 12125; Qiagen).

Example 3

Expression of Tick Chitinase Recombinant Protein in *Escherichia coli*

*Escherichia coli* JM109 (DE3) (Promega) was transformed with the recombinant plasmid prepared in Example 2, and then the transformants were cultured at 37° C. in an LB medium containing ampicillin. When $OD_{600\,nm}$ of the culture became 0.3~0.5, isopropyl-thio-galactoside (IPTG) was added to the culture so that the final concentration became 0.5 mmol/L, and then the transformants were further cultured at 37° C. for 4 hours.

The expression of tick chitinase recombinant protein was confirmed by carrying out 10% sodium dodecyl sulfate (SDS)-polyacrylamide gel electrophoresis [Laemmli et al., Nature, 227, 680-685 (1970)] followed by Coomassie staining.

As a result, the expression of the recombinant protein having a molecular weight of approximately 130 kDa was observed, and it was confirmed that the recombinant protein was a fusion protein of a GST leader protein (26 kDa) and the tick chitinase protein (104 kDa).

Example 4

Purification of Tick Chitinase Recombinant Protein and Preparation of Antiserum

The recombinant chitinase fusion protein expressed in *Escherichia coli* by the method described in Example 3 was purified in accordance with a protocol attached to a commercially available kit (Bulk GST Purification Module; Amersham Bioscience).

The result of electrophoresis of the purified recombinant chitinase fusion protein is shown in FIG. 1. In this connection, the electrophoresis and staining were performed in the manner similar to that described in Example 3. In FIG. 1, lane 1 is the result of molecular weight markers, lane 2 is the result of the purified recombinant chitinase fusion protein, and lane 3 is the result of the purified GST protein. The arrow at the right side of lane 3 indicates the recombinant chitinase fusion protein, and the numbers at the right side of lane 3 mean the molecular weights of the recombinant chitinase fusion protein (130 kDa), and the tick chitinase protein (104 kDa) and the GST leader protein (26 kDa) which are composed of the recombinant chitinase fusion protein.

An emulsion was prepared by mixing 200 μL of a solution containing 100 μg of the purified recombinant chitinase fusion protein with 200 μL of a complete Freund's adjuvant (Adjuvant Complete Freund; Difco). The emulsion was intraperitoneally inoculated into a 8-week-old female BALB/c mouse. After 2 and 4 weeks from the intraperitoneal inoculation, 100 μg of the recombinant chitinase fusion protein was mixed with an incomplete Freund's adjuvant (Difco), and each booster inoculation was carried out. After 2 weeks from the final inoculation, blood was collected and the resulting serum was kept at −20° C.

Example 5

Identification of Native (Wild Type) Chitinase by Immunoblotting

The wild type chitinase protein was identified by immunoblotting [Towbin et al., Proc. Natl. Acad. Sci. USA, 76, 4350-4354 (1979)] using the anti-recombinant chitinase fusion protein mouse serum obtained in Example 4. As samples, a lysate of tick eggs, i.e., a supernatant prepared in accordance with a method described in You et al., Insect Biochem. Mol. Biol., 32, 67-73 (2000), was used. More particularly, the lasate was prepared by homogenizing tick eggs in 20 mmol/L Tris-HCl and centrifuging the homogenate at 1000 rpm for 30 minutes.

The result is shown in FIG. 2. In FIG. 2, lane 1 is the result when the anti-recombinant chitinase fusion protein immune serum was used, and lane 2 is the result when the anti-GST protein immune serum was used (negative control). The arrow at the right side of lane 2 indicates the wild type chitinase protein, and the numbers at the right side of lane 2 mean molecular weights.

As shown in lane 1 in FIG. 2, the specific band of the wild type chitinase protein (114 kDa) was detected in the egg lysate. The measured molecular weight was approximately 10 kDa higher than the molecular weight (104 kDa) deduced from the amino acid sequence of SEQ ID NO: 2. The difference seems to be due to glycosylation.

Example 6

Confirmation of Chitinase Activity in Recombinant Chitinase Fusion Protein

In this Example, the chitinase activity in the recombinant chitinase fusion protein was examined on a 1% agarose gel containing 0.01% glycol chitin, in accordance with a known method for measuring the chitinase activity [Johannes et al., Infect. Immun., 69, 4041-4047 (2001)]. For comparison, the chitinase activity in Serratia marcescens chitinase (Sigma) or β-galactosidase was examined.

More particularly, 10 μL of each proten solution obtained by dissolving each protein in PBS (phosphate buffer) was added to each well in the agarose gel. After an incubation at 37° C. for 12 hours, the gel was stained in a 0.01% staining liquid (Fluorescent Brightener28; Sigma), washed with distilled water, and observed under an ultraviolet ray.

The recombinant chitinase fusion protein or Serratia marcescens chitinase reacted with chitin more strongly than did the β-galactosidase or PBS (control). As a result, it was confirmed that the recombinant chitinase fusion protein or Serratia marcescens chitinase exhibits a property of digesting chitin.

INDUSTRIAL APPLICABILITY

According to the polypeptide, polynucleotide, vector, transformant, and antibody of the present invention, the medicament of the present invention, particularly a tick vaccine, can be provided.

Further, according to the medicament of the present invention, particularly a tick vaccine, it is possible, for example, to exterminate ticks, or to treat or prevent tick-borne infections such as piroplasmosis, Q fever, or viral encephalitis.

Free Text in Sequence Listing

Each of the base sequences of SEQ ID NOS: 3, 4, 7, and 8 in the Sequence Listing is an artificially synthesized primer sequence.

In the base sequence of SEQ ID NO: 8 in the Sequence Listing, the alphabet "n" means A (i.e., adenine), C (i.e., cytosine), G (i.e., guanine), or T (i.e., thymine).

Although the present invention has been described with reference to specific embodiments, various changes and modifications obvious to those skilled in the art are possible without departing from the scope of the appended claims.

The invention claimed is:

1. An isolated polypeptide selected from the group consisting of:
   (a) a polypeptide consisting of the amino acid sequence of SEQ ID NO: 2;
   (b) a polypeptide comprising the amino acid sequence of SEQ ID NO: 2 and exhibiting chitinase activity; and
   (c) a polypeptide comprising an amino acid sequence having at least 90% homology with the amino acid sequence of SEQ ID NO: 2, and exhibiting chitinase activity.

2. A pharmaceutical composition comprising an isolated polypeptide selected from the group consisting of:
   (a) a polypeptide consisting of the amino acid sequence of SEQ ID NO:2;
   (b) a polypeptide comprising the amino acid sequence of SEQ ID NO:2 and exhibiting citinase activity; and
   (c) a polypeptide comprising an amino acid sequence having at least 90% homology with the amino acid sequence of SEQ ID NO:2, and exhibiting chitinase activity;
   and a pharmaceutically or veterinary acceptable carrier or diluent.

3. A method for screening a substance capable of modifying a chitinase activity of the polypeptide of claim 1, comprising the steps of:
   bringing the polypeptide into contact with a substance to be tested; and
   analyzing the chitinase activity of the polypeptide.

* * * * *

UNITED STATES PATENT AND TRADEMARK OFFICE
CERTIFICATE OF CORRECTION

PATENT NO. : 7,488,488 B2
APPLICATION NO. : 10/506010
DATED : February 10, 2009
INVENTOR(S) : Kozo Fujisaki et al.

It is certified that error appears in the above-identified patent and that said Letters Patent is hereby corrected as shown below:

On the Title Page, Item (73)
(73) Assignees:

Delete "Meui", insert -- Meiji --

Signed and Sealed this

Nineteenth Day of May, 2009

JOHN DOLL
*Acting Director of the United States Patent and Trademark Office*